(12) United States Patent
Boyce

(10) Patent No.: US 6,923,977 B1
(45) Date of Patent: Aug. 2, 2005

(54) SQUIRREL REPELLANT SYSTEM

(76) Inventor: Patricia Boyce, 405 Owis Nest Ct., Jackson, NJ (US) 08527

( * ) Notice: Subject to any disclaimer, the term of this patent is extended or adjusted under 35 U.S.C. 154(b) by 0 days.

(21) Appl. No.: 10/215,819

(22) Filed: Aug. 9, 2002

(51) Int. Cl.$^7$ .............................................. A01N 25/32
(52) U.S. Cl. ...................... 424/406; 424/405; 424/407; 424/731; 424/760; 514/546; 514/557
(58) Field of Search ................................ 514/920, 546, 514/557; 424/405–407, 410, 484, 485, 731, 424/760

(56) References Cited

U.S. PATENT DOCUMENTS

| | | | |
|---|---|---|---|
| 4,775,532 A | | 10/1988 | Clayton .................... 424/195.1 |
| 4,965,070 A | * | 10/1990 | Messina ...................... 424/581 |
| 5,466,459 A | | 11/1995 | Wilson ........................ 424/407 |
| 5,674,496 A | | 10/1997 | Etscorn et al. ........... 424/195.1 |
| 5,711,953 A | * | 1/1998 | Bassett ........................ 424/405 |
| 5,879,696 A | * | 3/1999 | Blumberg .................... 424/410 |
| 6,395,776 B1 | * | 5/2002 | Losel et al. .................. 514/531 |

\* cited by examiner

*Primary Examiner*—Neil S. Levy
(74) *Attorney, Agent, or Firm*—Goldstein Law Offices P.C.

(57) ABSTRACT

A non-toxic animal repellant system which may be used to prevent squirrels from entering residential or commercial buildings using a composition having castor oil, habanero pepper extract and white distilled vinegar. The composition may be sprayed onto surfaces or combined with petroleum jelly and applied to surfaces with a brush.

4 Claims, No Drawings

SQUIRREL REPELLANT SYSTEM

BACKGROUND OF THE INVENTION

1. Field of the Invention

The present invention relates to mixtures of naturally occurring, non-toxic, and environmentally safe substances which may be used to prevent squirrels from destroying property and entering homes and other structures.

2. Description of Related Art

Squirrels and other rodents cause many millions of dollars of economic damage every year by entering residences and other dwellings and destroying property. Squirrels also damage electrical wires, siding on buildings, ornamental trees and shrubs, garden bulbs, outdoor furniture and other property. They enter into buildings and build nests in which they live and raise their young. The most effective way of keeping a residence free of squirrels is to keep them from entering in the first place. Once they enter, it is very hard to persuade them to leave.

Various mixtures have been formulated which have been used to repel squirrels and other rodents from eating planted bulbs and bird seed or from foraging through bags of garbage which contain edible material. Traditional methods of repelling squirrels include the use of a variety of chemical repellents. Some of these are napthalene-based products (e.g. RID-A-CRITTER, RO-PEL or HINDER) which are poisonous to humans, and as such, they are limited in usage to locations where they are not likely to cone into contact with humans or food. In particular, HINDER and RO-PEL cannot be used in areas which may be accessible to children.

In addition, these products are applied to planted vegetable matter and are only effective for approximately one month. Accordingly, they must be reapplied approximately every month in order to be effective.

Accordingly, available formulations which are effective in preventing squirrels from entering buildings or destroying other property are generally both toxic to humans and pets and environmentally hazardous. Mixtures which are effective in deterring squirrels and other rodents from eating planted bulbs are toxic to humans or to household pets and would not be as useful for the owners of buildings. Thus, a repellant which is environmentally safe would have even greater utility.

Furthermore, no effective and safe repellant exists which may be conveniently applied to surfaces either by spraying or by spreading onto a surface with a brush, thereby giving the user flexibility in applying the repellant.

U.S. Pat. No. 4,175,532 by Clayton discloses an animal repellant composition comprising an animal repellant carried by a vehicle comprising a di(alkhyl) adipate and a method of repelling animals. Clayton mentions that one of several possible animal repellants that can be used is essence of red pepper. However, Clayton is specifically intended for application of the repellant composition to the outside of containers holding edible refuse. Clayton even contemplates mixing the composition with the refuse itself. Accordingly, Clayton is aimed specifically at protecting refuse from animal tampering.

U.S. Pat. No. 5,466,459 by Wilson discloses a wax and capsaicin-based pesticide which is applied to a host plant. U.S. Pat. No. 5,879,696 by Blumberg discloses a method of preventing animals from eating bird seed which consists of treating the bird seed with capsaicin. However, providing a natural component in bird seed, which is to be consumed directly by an animal we do not wish to harm makes sense in the context of Blumberg, but does not teach its suitability as an effective repellant compared to other available repellants which are not intended to be consumed in a non-harmful way. Accordingly, both Wilson and Blumberg disclose products intended for very specific applications.

U.S. Pat. No. 5,674,496 by Etscorn discloses a detailed method for preparing an animal repellant extract which contains capsaicinoid. However, Etscorn seems particularly aimed at preventing rodent damage to insulation which protects electrical and fiber-optic cables.

While these formulations and methods may be suitable for the particular purposes described, they would not be as suitable for the purposes of the present intention as disclosed hereafter.

SUMMARY OF THE INVENTION

It is an object of the invention to repel squirrels and other rodents from entering and/or doing damage to homes and other buildings. Accordingly, a mixture is provided which is effective both in repelling squirrels living within a building and deterring the squirrel from entering and nesting within the building.

It is another object of the invention that the product may be used by homeowners and businesses without a special license which may generally be required for the application of other substances. Accordingly, the product is typically suitable for non-licensed consumer use because it does not kill the squirrels and is not toxic to humans.

It is a further object of the invention to provide a substance that will not need to be applied frequently in order to continue to be effective in repelling animals. Accordingly, the oil base allows it to be spread on surfaces, resist freezing during cold weather, and thus remain effective for an extended period of time.

It is a further object of the invention to provide a substance which can be effectively used by homeowners to dissuade squirrels from nesting in areas that they prefer such as attics. Accordingly, due to its consistency, the composition may be applied directly onto surfaces, and because of its non-toxicity it can be used in direct proximity to areas where humans dwell.

It is a further object of this invention to provide a user with a choice of method of application of the mixture. A user may apply this formulation either by thinning it and spraying it onto a surface or by mixing it with petroleum jelly and spreading it onto the surface with a brush. The latter method of application has the added advantage of making the composition less water soluble and therefore, more long lasting, even after exposure to rain, and after encountering freezing temperatures.

It is a further object of this invention to provide the user with a product which is environmentally safe and which can be easily removed from surfaces with soap and water. Accordingly, the oil base allows the use of an emulsifying agent such as soap to allow the easy removal of the substance when desired.

The invention is a non-toxic animal repellant system which may be used to prevent squirrels from entering residential or commercial buildings using a composition having castor oil, habanero pepper extract and white distilled vinegar. The composition may be sprayed onto surfaces or combined with petroleum jelly and applied to surfaces with a brush.

DETAILED DESCRIPTION OF THE PREFERRED EMBODIMENTS

The present invention is directed to a squirrel repellant, which is a mixture of naturally occurring substances which may be applied to surfaces in order to prevent squirrels from entering homes or other structures, and to encourage them to leave the structure if they have already nested therein. The naturally occuring substances are selected to act upon the various senses of the squirrels. In particular, various components are provided which seek to negatively impact the squirrels sense of smell, be distasteful to the squirrel, and even irritating to the skin of the squirrel. What is contemplated is primarily a mixture comprising habanero pepper extract, castor oil, and vinegar. Habanero pepper extract is defined as the capsaicin-containing extract of dried habanero peppers. The vinegar serves to enhance the negative flavor aspects of the habanero pepper extract. The castor oil both has a negative smell and acts as an oil base to prevent the composition from freezing during cold weather.

Further, xantham gum may be included in the composition to increase the scent, touch, and taste deterrence properties of the composition.

Preferably these substances are combined in the proportion of 2 parts castor oil to 1 part white distilled vinegar, and to further include 2–5% habanero pepper extract. Additionally, the addition of xantham gum is preferably at 0.05% of the composition. Also contemplated is the addition of salt, preferably at 0.05% of the composition.

The preferred manner of application of the substance in order to achieve optimum efficiency is to either suitably thin (if necessary) and spray the above mixture onto the surface of a structure or to bland the mixture with petroleum jelly and to spread it onto a surface with a brush.

The mixture which includes petroleum jelly would be more appropriate for areas which are exposed to water which will dissolve the active ingredients of the repellant. Additionally, the presence of petroleum jelly causes the product to adhere to the squirrel's paws, where it would cause a minor burning sensation, and therefore makes it a more effective deterrent. The castor oil serves three functions. One is to enhance the repellant characteristics of the mixture, as squirrels do not like its smell. The second function is to provide an oil base which enhances the ability to apply the mixture in spray form or by brushing it onto a surface. Lastly, the addition of the oil prevents the mixture from freezing at temperatures typically encountered during the winter months, during which squirrels continue to be active and are most likely to seek out a nest within a heated dwelling.

This invention has been tested by the inventor and proven to be effective. It has been applied to areas of a roof that had been repeatedly used by squirrels to enter into a home. Immediately upon use, no re-entry of squirrels into the unit were observed. The product continued to be effective over a period of two months, during which there were three snowstorms and several rains, including a rainfall of several inches.

In conclusion, herein is presented a mixture of natural products that is both non-toxic and environmentally safe and is effective in deterring squirrels from entering buildings and destroying other property. The mixture is applied to surface areas associated with homes and buildings. These areas include roof areas, siding, gutters, vents, and soffits. The mixture is non-toxic to humans or rodents. Additionally, it is environmentally safe. The invention is described by example throughout the written description. It should be understood that numerous variations are possible, while adhering to the inventive concept. Such variations are contemplated as being a part of the present invention.

What is claimed is:

1. A squirrel repellant comprising:
    (a) habanero pepper extract;
    (b) castor oil;
    (c) vinegar;
    (d) xanthan gum; and
    (e) salt;
wherein the ratio of the volumes of the components in the whole composition is 2–5% habanero pepper extract: 60–64% castor oil: 30–32% vinegar, and wherein the presence of xanthan gum and salt are optional.

2. The squirrel repellant as recited in claim 1, wherein the xanthan gum is present in a weight percent of 0.05% of the weight of the whole composition.

3. The squirrel repellant as recited in claim 2, wherein the salt is present in a weight percent of 0.05% of the weight of the whole composition.

4. The squirrel repellant as recited in claim 3, further comprising a petroleum jelly base, wherein the components are combined in the petroleum jelly base for ease of application onto an existing surface.

* * * * *